(12) United States Patent
Manker et al.

(10) Patent No.: US 7,089,064 B2
(45) Date of Patent: Aug. 8, 2006

(54) THERAPEUTIC PROSTATIC THERMOTHERAPY

(75) Inventors: Charles F. Manker, Lake Forest, IL (US); Aaron P. Perlmutter, New York, NY (US); Theron N. Schaefermeyer, North Salt Lake, UT (US); Dixie T. Sells, Sandy, UT (US); Paul F. Turner, North Salt Lake, UT (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 10/232,062

(22) Filed: Aug. 30, 2002

(65) Prior Publication Data

US 2003/0023238 A1    Jan. 30, 2003

Related U.S. Application Data

(62) Division of application No. 09/766,746, filed on Jan. 22, 2001, now Pat. No. 6,522,931.

(51) Int. Cl.
*A61F 2/00* (2006.01)
(52) U.S. Cl. ........................................ 607/102; 606/34
(58) Field of Classification Search ............ 606/27–31, 606/34, 35, 41, 42; 607/101, 102
See application file for complete search history.

(56) References Cited

U.S. PATENT DOCUMENTS

| | | | |
|---|---|---|---|
| 2,936,761 A | 5/1960 | Snyder | |
| 3,720,199 A | 3/1973 | Rishton et al. | |
| 3,978,863 A | 9/1976 | Fettel et al. | |
| 4,046,139 A | 9/1977 | Horn | |
| 4,154,246 A | 5/1979 | LeVeen | |
| 4,275,730 A | 6/1981 | Hussein | |
| 4,311,154 A | 1/1982 | Sterzer et al. | |
| 4,312,364 A | 1/1982 | Convert et al. | |
| 4,403,618 A | 9/1983 | Turner et al. | |
| 4,448,198 A | 5/1984 | Turner | |
| 4,462,412 A | 7/1984 | Turner | |
| 4,469,103 A | 9/1984 | Barrett | |
| 4,522,194 A | 6/1985 | Normann | |
| 4,524,550 A | 6/1985 | Burke et al. | |
| 4,583,556 A | 4/1986 | Hines et al. | |
| 4,586,516 A | 5/1986 | Turner | |

(Continued)

FOREIGN PATENT DOCUMENTS

DE        2815156        10/1978

(Continued)

OTHER PUBLICATIONS

"Critical Evaluation of Treatment Modalities in Local Hyperthermia of the Prostate" pp. 336-337 in Benign Prostate Hyperplasia: Innovations in Management, Petrovich & Baert (Eds.) Springer Verlag Publishing (1994).

(Continued)

*Primary Examiner*—Michael Peffley
(74) *Attorney, Agent, or Firm*—Jose' W. Jimenez

(57) ABSTRACT

The present invention provides a method of treating a prostate in a patient in need thereof and a heating catheter, or an electromagnetic radiation applicator, system suitable for effecting the present inventive method. The present inventive method provides for substantial unexpected improvement in patient outcome by providing, inter alia, a preferred therapeutic temperature for thermotherapy of the prostate and a method of decreasing a patient's intolerance due to pain. The present inventive system provides for, inter alia, automatic implementation of the present inventive method.

15 Claims, 4 Drawing Sheets

U.S. PATENT DOCUMENTS

| | | | |
|---|---|---|---|
| 4,589,423 A | 5/1986 | Turner | |
| 4,601,296 A | 7/1986 | Yerushalmi | |
| 4,632,669 A | 12/1986 | Phipps, Sr. et al. | |
| 4,638,813 A | 1/1987 | Turner | |
| 4,658,836 A | 4/1987 | Turner | |
| 4,662,383 A | 5/1987 | Sogawa et al. | |
| 4,669,475 A | 6/1987 | Turner | |
| 4,672,980 A | 6/1987 | Turner | |
| 4,676,258 A | 6/1987 | Inokuchi et al. | |
| 4,681,122 A | 7/1987 | Winters et al. | |
| 4,700,716 A | 10/1987 | Kasevich et al. | |
| 4,712,559 A | 12/1987 | Turner | |
| 4,790,821 A | 12/1988 | Stines | |
| 4,798,215 A | 1/1989 | Turner | |
| 4,813,429 A | 3/1989 | Eshel et al. | |
| 4,860,744 A | 8/1989 | Johnson et al. | |
| 4,860,752 A | 8/1989 | Turner | |
| 4,891,483 A | 1/1990 | Kikuchi et al. | |
| 4,967,765 A | 11/1990 | Turner et al. | |
| 4,974,587 A | 12/1990 | Turner et al. | |
| 5,003,991 A | 4/1991 | Takayama et al. | |
| 5,007,437 A | 4/1991 | Sterzer | |
| 5,045,051 A | 9/1991 | Milder et al. | |
| 5,056,528 A | 10/1991 | Zytkovicz et al. | |
| 5,057,105 A * | 10/1991 | Malone et al. | 606/28 |
| 5,097,844 A | 3/1992 | Turner | |
| 5,197,940 A | 3/1993 | Sievert et al. | |
| 5,209,725 A | 5/1993 | Roth | |
| 5,220,927 A | 6/1993 | Astrahan et al. | |
| 5,234,004 A | 8/1993 | Hascoet et al. | |
| 5,249,585 A | 10/1993 | Turner et al. | |
| 5,300,099 A | 4/1994 | Rudie | |
| 5,344,435 A | 9/1994 | Turner et al. | |
| 5,354,325 A | 10/1994 | Chive et al. | |
| 5,366,490 A | 11/1994 | Edwards et al. | |
| 5,531,676 A | 7/1996 | Edwards et al. | |
| 5,542,916 A | 8/1996 | Hirsch et al. | |
| 5,571,153 A | 11/1996 | Wallsten | |
| 5,599,301 A | 2/1997 | Jacobs et al. | |
| 5,616,114 A | 4/1997 | Thornton et al. | |
| 5,620,480 A | 4/1997 | Rudie | |
| 5,628,771 A * | 5/1997 | Mizukawa et al. | 607/102 |
| 5,735,846 A * | 4/1998 | Panescu et al. | 606/41 |
| 5,941,898 A | 8/1999 | Moenning et al. | |
| 5,971,973 A | 10/1999 | Peters | |
| 5,980,485 A | 11/1999 | Grantz et al. | |
| 6,122,551 A * | 9/2000 | Rudie et al. | 607/102 |
| 6,162,217 A * | 12/2000 | Kannenberg et al. | 606/34 |
| 6,183,468 B1 * | 2/2001 | Swanson et al. | 606/40 |
| 6,216,703 B1 | 4/2001 | Manker et al. | |

FOREIGN PATENT DOCUMENTS

| | | |
|---|---|---|
| DE | 3534124 | 4/1987 |
| EP | 0105677 | 4/1984 |
| EP | 0370890 | 5/1990 |
| SU | 1512-622 | 10/1989 |
| WO | WO 81/03616 | 12/1981 |
| WO | WO 89/11311 | 11/1989 |
| WO | WO 97/01374 | 1/1997 |
| WO | WO 99/58194 | 11/1999 |

OTHER PUBLICATIONS

Baert et al. "Transurethral Microwave Hyperthermia for Benign Prostatic Hyperplasia: The Leuven Clinical Experience" Journal of Endourology, vol. 7 (No. 1) pp. 61-69 (1993).

Baert et al. "Transurethral Microwave Hyperthermia for Benign Prostatic Hyperplasia: Preliminary Clinical and Pathological Results" The Journal of Urology, vol. 144, pp. 1383-1387 (Dec. 1990).

"Treatment Results with Transurethral Hyperthermia in Patients with Benign Prostatic Hyperplasia" pp. 317-327 in Benign Prostate Hyperplasia: Innovations in Management, Petrovich & Baert (Eds.) Springer Verlag Publishing (1994).

Bernier et al. "Thermal Therapy in the Treatment of Benign Prostatic Hyperplasia" Current Opinion in Urology, vol. 7, pp. 15-20 (1997).

Bhanot et al. "A Radiofrequency Method of Thermal Tissue Ablation for Benign Prostatic Hyperplasia" Urology, vol. 45 (No. 3) pp. 427-434 (Mar. 1995).

Carter et al. "Single-Session Transurethral Microwave Thermotherapy for the Treatment of Benign Prostatic Obstruction" Journal of Endourology, vol. 5 (No. 2) pp. 137-144 (1991).

Corica et al. "Transurethral Radio Frequency Thermotherapy for Syptomatic Benign Prostatic Hyperplasia" EurUrol, vol. 23, pp. 312-317 (1993).

De la Rosette et al. "Current Status of Thermotherapy of the Prostate" The Journal of Urology vol. 157, pp. 430-438 (Feb. 1997).

Diederich et al. "Combination of Implantable and Transurethral Ultrasound Applications for Prostate Thermal Therapy" Proceedings of the 1997 IEEE Ultrasonics Symposium, Ontario, Canada, Oct. 5-8, 1997. vol. 2, pp 1337-1340 (Oct. 5, 1997).

Devonec et al. "Transurethral Microwave Heating of the Prostate—Or from Hyperthermia to Thermotherapy" Journal of Endourology, vol. 5 (No. 2) pp. 129-135 (1991).

Devonec et al. "Review: Transurethral Microwave Thermotherapy in Benign Prostatic Hyperplasia" Journal of Endourology, vol. 7 (No. 3) pp. 255-259 (1993).

Devonec et al. "Transurethral Microwave Thermotherapy (TUMT)" 1992 Monographs in UrologyTM, vol. 13 (No. 4) pp. 77-95. Stamey, Thomas A., Editor.

Sapozink et al. "Transurethral Hyperthermia for Benign Prostatic Hyperplasia: Preliminary Clinical Results" The Journal of Urology, vol. 143, pp. 944-950 (May 1990).

Vandenbossche et al. "(TURF) Transurethral Radiofrequency Heating for Benign Prostatic Hyperplasia at Various Temperatures with Thermax II,: Clinical Experience" Eur Urol, vol. 23, pp. 302-306 (1993).

Viguier et al. "Benign Prostatic Hypertrophy Treatment by Transurethral Radiofrequency Hyperthermia with Thermex II" Eur Urol, vol. 23, pp. 318-321 (1993).

Baba et al., Journal of Endourology, 6 (5): 371-376 (1992).

Beaven et al., Urology,__: 251-254 (1992) in Prostatron 1997 Thermotherapy Compendium (Re-Published by EDAP Technomed, Inc. Cambridge, Mass.).

Blute, 3 pages Reprinted From A.U.A. Today, 6(11) (1993) in Prostatron 1997 Thermotherapy Compendium (Re-Published by EDAP Technomed, Inc. Cambridge, Mass.).

Blute et al., The Journal of Urology, 150: 1591-1596 (1993).

Blute, Seminars in Urology, XII(3): 181-191 (1994).

Devonec et al., Eur. Urol. 23: 267-274 (1993).

Devonec et al., Curr. Opinion in Urology, 5: 3-9 (1995).

Devonec et al., Curr. Opinion in Urology, 3:202-208 (1993).

De Wildt et al., British Journal of Urology, 76: 531-538 (1995).

Hofner et al., "Changes In Outflow Obstruction Following Transurethral Microwave Thermotherapy," (Original Source Unknown) (1995) in Prostatron 1997 Thermotherapy Compendium (Re-Published by EDAP Technomed, Inc. Cambridge, Mass.).

Homma et al., Journal of Endourology, 7: 261-265 (1993).

Perlmutter, "Prostatic Heat Treatments" in Alternate Methods in the Treatment of Benign Prostatic Hyperplasia (Romas and Vaughan, Eds.) pp. 135-155 (1993).

Tubaro et al., Eur. Urol. 23: 285-291 (1993).

Walden et al., British Journal of Urology, 81: 817-822 (1998).

Watson et al., World Journal of Urology, 9: 7-11 (1991).

Astrahan et al., "Microwave Applicator for Transurethral Hyperthermia of Benign Prostate Hyperplasia", International Journal of Hyperthermia, 5, (3), pp. 283-296 (May/Jun. 1989).

Constable et al, "Perturbation of the Temperature Distribution in Microwave Irradiated Tissue Due to the Presence of Metallic Thermometers", Med. Phys., 14 (3) pp. 385-388 (May/Jun. 1987).

Diederich et al., "Induction of hyperthermia Using an Intracavitary Multielement Ultrasonic Applicator," IEEE Transactions on Biomedical Engineering, 36 (4), (Apr., 1989).

Ding Jen Lee, et al., "A New Design of Microwave Interstitial Applicators for Hyperthermia with Improved Treatment Volume", Int. J. Radiation Oncology Biol. Phys, 12, pp. 2003-2008 (Nov. 1986).

Ding-Jiu Li, et al., "Design & Thermometry of an Intracavitary Microwave Applicator Suitable for Treatment of Some Vaginal & Rectal Cancers", Int. J. Radiation Oncology Boil. Phys., 10, pp. 2155-2161 (Nov. 1984).

Dunscomde et al., "Heat Production in Microwave-Irradiated Thermocouples", Med. Phys. 13 (4), pp. 457-461 (Jul./Aug. 1986).

El-Deek M. El-Sayed et al., "Use of Sheath Helix Slow-Wave Structure as an Applicator in Microwave Heating Systems", Journal of Microwave Power, 16 (3 and 4), pp. 283-288 (1981).

Harada, et al., "Microwave Surgical Treatment of Diseases of Prostate", Urology, 26 (6), pp. 572-576 (Dec. 1985).

IEEE Transactions on Biomedical Engineering, 36 (4), 432-438 (1989).

Leybovich, et al., "Intracavitary Hyperthermia: A Newly Designed Applicator for Tracheal Tumors", Endocurietherapy/Hyperthermia Oncology, 3, pp. 23-29 (Jan. 1987).

Lindner et al., "Local Hyperthermia of the Prostate Gland for the Treatment of Benign Prostatic Hypertrophy and Urinary Retention" British Journal of Urology, 1987, 60, pp. 567-571.

McGuire, R. "Transurethral Hypertermia for BPH: Trial's Goal is to Top 80% Success," Medical Tribune, 29 (9), pp. 3, 13, 14 (Mar. 31, 1988).

ProstaLund, "ProstaLund Feedback Treatment of BPH", www.prostalund.com.

ProstaLund, "About BPH" www.prostalund.com.

Mendecki et al., "Microwave Applicators for Localized Hyperthermia Treatment of Cancer of the Prostate", Int. J. Radiation Boil. Phys., (11), pp. 1583-1588 (Nov. 1980).

Satoh et al., "Thermal Distribution Studies of Helical Coil Microwave Antennas for Interstitial Hyperthermia, "Int'l J. Radiation Oncology Biol. Phys., 15, pp. 1209-1218

Taylor et al., "Electromagnetic Syringe" IEEE Transactions on Biomedical Engineering, BME 25 (3) (May, 1978).

Wu, et al., "Performance Characteristics of a Helical Microwave Interstitial Antenna for Local Hyperthermia", Med. Phys, 14(2), pp. 235-237 (Mar./Apr. 1987).

Yerushalmi, et al., "Localized Microwave Hypertermia in the Treatment of Poor Operative Risk Patients with Benign Prostatic Hyperplasia", Williams & Wilkins, Co. vol. 133, pp. 873-876 (May 1985).

* cited by examiner

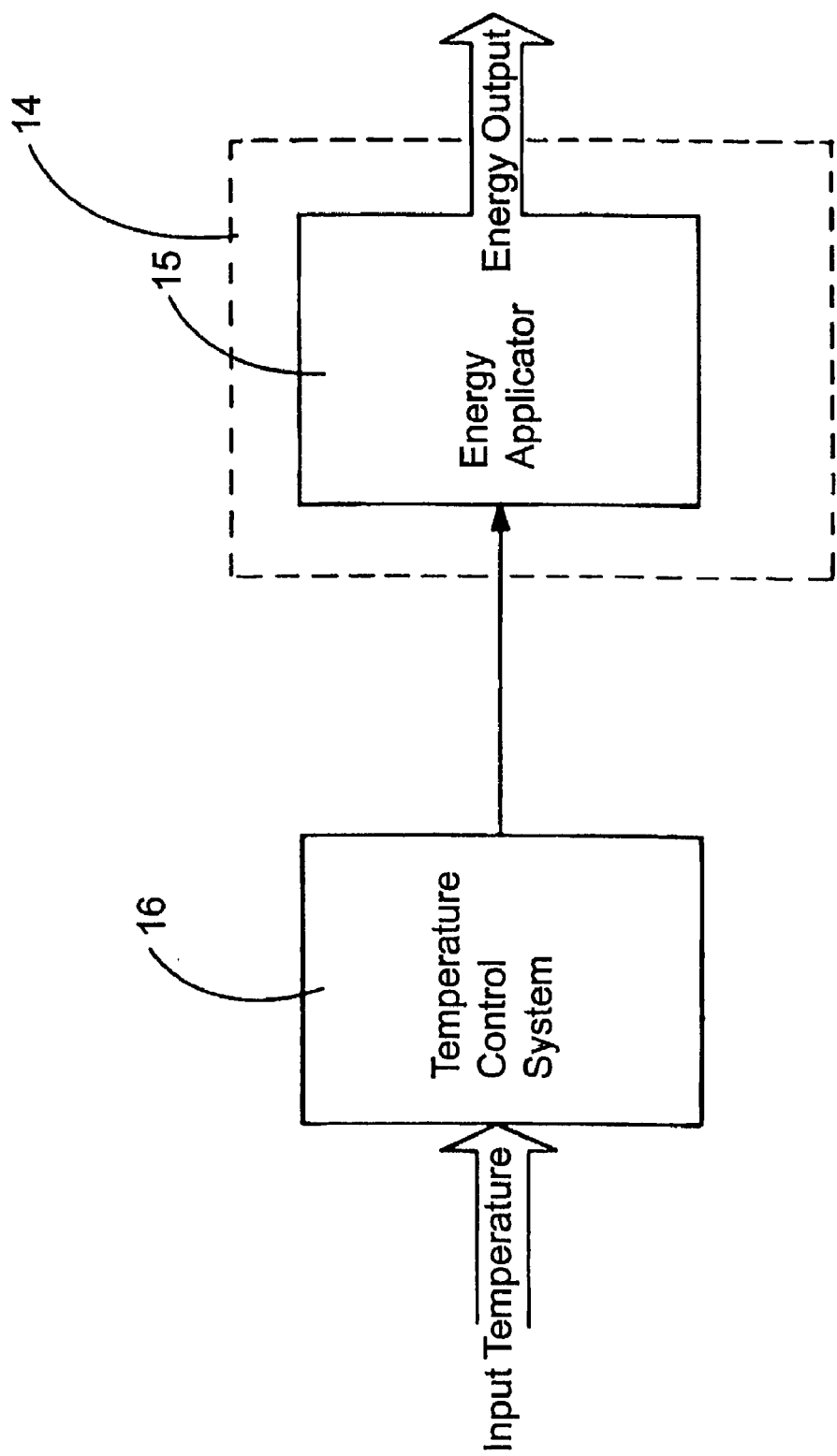

THERAPEUTIC PROSTATIC THERMOTHERAPY

CROSS-REFERENCE TO RELATED APPLICATION

This application is a divisional of U.S. Patent application Ser. No. 09/766,746, filed on Jan. 22, 2001 now U.S. Pat. No. 6,522,391, issued on Feb. 18, 2003, entitled "THERAPEUTIC PROSTATIC THERMOTHERAPY", incorporated herein by reference in its entirety.

TECHNICAL FIELD OF THE INVENTION

The present invention relates to the heat treatment of prostate disorders, including, but not limited to, benign prostatic hyperplasia, prostatitis, and prostatic malignancy.

BACKGROUND OF THE INVENTION

Use of heating or energy radiating devices, particularly microwave radiating devices, to administer heat for the treatment of various diseases of the prostate have been demonstrated to provide efficacious treatment of various prostate conditions (Devonec et al., *Monographs in Urology,* 13, 77–95 (1992); De La Rosette et al., *J. Urology,* 157, 430–438 (1997); Devonec et al., *J. Endourology,* 5, 129–135 (1991); Bernier et al., *Curr. Opin. Urol.,* 7, 15–20 (1997)). Research has indicated that the cellular transformations brought about by raising tissue temperatures above certain levels can be used therapeutically. At temperatures above 45° C., thermal damage has been found to occur to cells, even when the exposure to the elevated temperatures lasts for even a short period of time. Thermal therapy has been defined as the process of heating tissue to greater than 45° C. to create necrosis. Both normal and abnormal cells respond to thermal exposure. Accordingly, therapies using heat have relied on healthy tissue regeneration after the delivery of a "thermal dose." A thermal dose is a quantity which is indicative of the biological impact of elevated temperature maintained for a period of time. For the purposes of the present invention, thermal dosages can be calculated according to the method of Sapareto et al., *International Journal of Radiation Oncology, Biology, Physics,* 10, 787–800 (1984), except that the breakpoint of 45° C., rather than 43° C. is used for non-malignant tissues. That is, for the purposes of the present invention, thermal dose measured in Equivalent 45° C. hours is equal to the sum of the products of one half of the treatment temperature in excess of 45° C. times the duration at that time, or $$\sum_{t=0}^{t=final} 0.5^{(45-T)} \Delta t,$$

wherein T is temperature in degrees centigrade and t is time in hours.

A variety of different methods have been developed to deliver therapeutically effective quantities of heat to the prostate, including ultrasound delivery devices, RF delivery devices and hot water-recirculating catheters. One such device is the "WITT" hot water recirculating catheter, which is manufactured by ArgoMed, Inc. of Parsippany, N.J. (USA). Another such device is the "Thermex II", which is manufactured by Direx Systems, Ltd. While hot water recirculating catheters are useful in the context of the present invention, a significant drawback is that it is difficult to apply an accurate thermal dose to the prostatic urethra while simultaneously avoiding delivery of a therapeutic dose of heat to non-target tissues such as the penis. Moreover, the design of hot water recirculating catheters can make accurate placement of the heating zones within the patient more difficult. A limitation to the usage of RF applicators is their relatively poor ability to penetrate tissue, often resulting in superficial treatment of the prostatic tissue.

A more preferred method to deliver thermotherapy in the context of the present invention is via a urethrally-inserted catheter with an imbedded microwave antenna. A cooling device is typically incorporated into microwave emitting catheters so that urethral tissue proximal to the microwave antenna is cooled. The addition of this feature has been directed at preserving the prostatic urethra, thereby reducing treatment discomfort and post-treatment recovery time. A temperature or energy measurement device can be used during treatments so that a thermal dose can be measured. Treatments utilizing this approach include TransUrethral Microwave Thermotherapy (TUMT). One disease currently treated by TUMT is Benign Prostatic Hyperplasia (BPH). The therapeutic effect of such therapies can be measured in any suitable manner. For example, therapy can be measured by an improvement in the AUA symptom score, or by an improvement in the Madsen-Iversen score, an improvement in urine flow, an improvement in urethral diameter, or the like.

The objective of TUMT of BPH is to destroy a portion of the prostatic tissue, while preserving the tissue immediately adjacent to the prostatic urethra and the tissue immediately adjacent to the same. Current opinion in the field is that the greater the tissue destruction in the prostate, the more beneficial the treatment (De La Rosette et al., supra). Therefore, current device and therapy design is directed at improving the maximum heat dose over the shortest period of time. In that regard, typical maximum temperatures frequently reach 65° C. or greater within the prostate. Unfortunately, this has a number of undesirable side-effects. For example, with prior art TUMT methods, hematuria rates typically exceed 30%, rates of urinary retention requiring long term catheterization usually exceeds 20%, rates of urethral bleeding not merely due to catheterization exceed 5%, and rates of urinary tract infection, ejaculator disturbances, inflammation in the urethra, chronic incontinence, and impotence are all statistically significant and exceed about 1.5%.

There are, however, other delivery methods which utilize non-cooled radiation applicators and require the delivery of multiple treatments at relatively low temperatures (45° C.–47° C. and lower). The objective of these methods is to obtain a therapeutic benefit while avoiding temperature ranges that are commonly thought to cause patient intolerance and give rise to significant side effects. The problem with these methods is that the data suggest, and current published opinion in the art states, that efficacy is reduced. In addition, multiple treatment sessions are required at these relatively low temperatures which is inconvenient and uncomfortable for the patient and economically disadvantageous for the physician.

One significant drawback to other TUMT devices and therapies is that they are frequently painful for the patient and require the use of narcotic analgesics to control pain. This makes current TUMT inconvenient, limits the use of the therapy, adds to the expense and recovery time, and can potentially result in patient loss.

A further drawback to other TUMT devices is the requirement for multiple treatment sessions and its limited efficacy. Thus, the economics of the treatment are severely limited.

The electromagnetic radiation applicator systems developed for the treatment of BPH have limited the ability of the skilled artisan to control urethral and prostate temperatures. Many prior art radiation applicator devices have controlled the heating of the prostate by simply controlling the power supplied to the heating unit. This method of controlling the heating is typically necessary when the catheter system is used in conjunction with a surface cooling device, because the surface cooling device alters measured temperatures. Non-cooled catheter systems (see, e.g., U.S. Pat. No. 4,967,765 to Turner et al.) have the ability to monitor surface temperatures more accurately than cooled catheter systems. However, these devices have also been constructed in a manner to limit complexity and cost. Accordingly, prior art catheter systems have been capable of heating tissue to a pre-selected temperature and maintaining the tissue at that temperature, but have not incorporated the more advanced features of the present invention. Other catheter designs useful in the context of the present inventive system have been commercially developed, e.g., by EDAP/Technomed and Urologix. While these other catheter designs are well known in the art, other examples are disclosed, e.g., by U.S. Pat. Nos. 4,620,480 and 5,628,770.

In view of the foregoing problems, there is a need for prostatic thermotherapy, particularly for BPH that is cost-effective, eliminates the use of general anesthesia and obviates the need for a cooled catheter. There is also a need for a prostatic thermotherapy that reduces non-beneficial side effects of previous methods.

The present invention provides such a method and related devices. These and other advantages of the present invention, as well as additional inventive features, will be apparent from the description of the invention provided herein.

BRIEF SUMMARY OF THE INVENTION

The present invention provides a method of heat treating a patient's prostate tissue and devices, programs, and systems useful in practicing the present inventive method.

Surprisingly, it has now been found that the maximum urethral temperature that can be tolerated by patients to whom narcotic analgesics or general anesthesia have not been administered exceeds the previously art-accepted maximum of 45° C.–47° C., under selected conditions. It has also now been found that the side-effects which have been reported to accompany high temperature treatment of the prostate are substantially reduced by use of the method of the present invention when the maximum urethral temperature is kept below about 57° C. Moreover, it has been surprisingly discovered that preservation of the prostatic urethra is not an important parameter of the thermotherapy of the prostate. On the contrary, the urethra and the urethrally proximal portions of the prostate are the tissues in which heating is desired in the present inventive method. Thus, the present invention provides a method of heat treating a patient's prostate tissue wherein the temperature of the prostate tissue is raised from an initial temperature below the destination temperature, to a destination temperature in the range of from 49° C. to almost 57° C. The destination temperature is maintained for a period of time sufficient to administer a sufficient amount of heat to achieve a therapeutic effect on the prostate.

It has now been found that by allowing a patient to acclimatize to elevated urethral temperatures the patient's threshold of pain, with or without antiinflammatory analgesics, is elevated to about 60° C. Thus, the present invention provides a method of prostatic thermotherapy wherein the maximum urethral temperature is raised to an elevated temperature which exceeds the previous art-accepted maximum by elevating the method temperature in such a manner so as to allow the patient to acclimatize the temperature elevation procedure. The rate at which the temperature can be raised from 37° C. to the range of about 42° C. and 46° C. can be relatively rapid. In keeping with the inventive method, it is desirable for the rate at which temperature is elevated from about 44° C. to the destination temperature to occur more slowly. Further, the rate of rise in temperature preferably decreases as the maximum urethral temperature approaches the destination temperature. In general, the rate of increase in temperature according to the present invention varies between 1° C. per 0.5 minutes to 1° C. per 15 minutes. In order to allow better patient acclimatization, the rate of change in the temperature preferably does not exceed 1° C. per minute, and more preferably does not exceed 1° C. per 2 minutes. However, it is desirable to physician and patient to minimize the amount of time required for therapy. In order to reduce the amount of time required to acclimate the patient to elevated urethral temperatures, the rate of temperature rise can be increased to 1° C. per 10 minutes near the destination temperature and to about 1° C. per 2 minutes at the lower temperatures. The total time to raise the urethral temperatures from 37° C. to the destination temperature preferably ranges from 15 minutes to 2 hours, and more preferably is from 20 to 45 minutes. Moreover, it will be appreciated that the temperature rise can be continuous or discontinuous (i.e., "stepped").

The invention can best be understood with reference to the accompanying drawings and in the following detailed description of the preferred embodiments.

BRIEF DESCRIPTION OF THE DRAWINGS

FIG. 4 is a block diagram of a urethral insertable applicator system suitable for carrying out the present inventive method.

DESCRIPTION OF THE PREFERRED EMBODIMENTS

Figure 1:
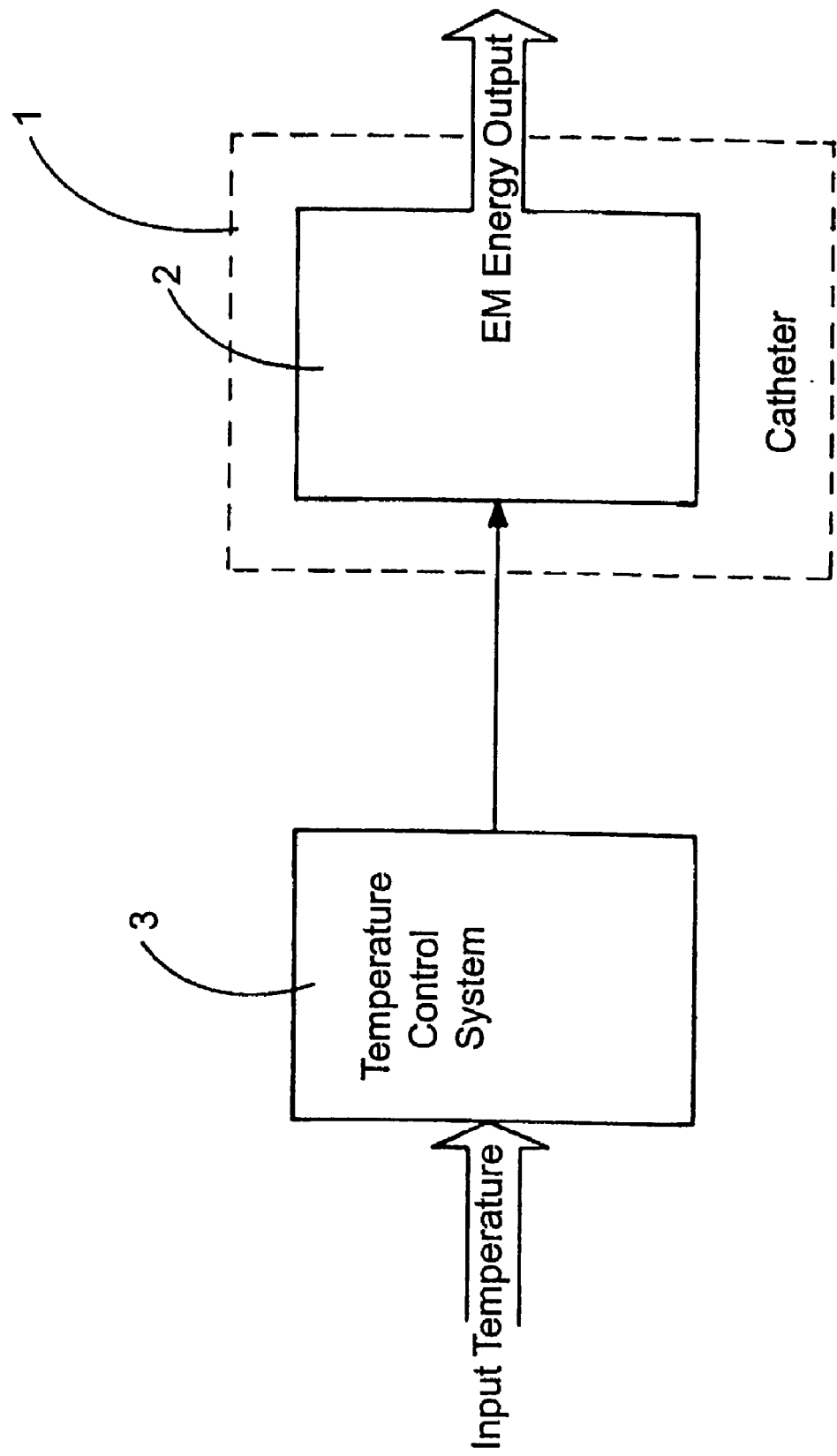
FIG. 1 is a block diagram of a urethral insertable electromagnetic radiation applicator system according to an embodiment of the present invention.

The present invention provides a method of heat treating a patient's prostate tissue and devices, programs, and systems useful in practicing the present inventive method.

Surprisingly, it has now been found that the maximum urethral temperature that can be tolerated by patients to whom narcotic analgesics or general anesthesia have not been administered exceeds the previously art-accepted maximum of 45° C.–47° C., under selected conditions. It has also now been found that the side-effects which have been reported to accompany high temperature treatment of the prostate are substantially reduced by use of the method of the present invention when the temperature is kept below about 57° C. Moreover, it has been surprisingly discovered that preservation of the prostatic urethra is not an important parameter of the thermotherapy of the prostate. On the contrary, the urethra and the urethrally proximal portions of the prostate are the tissues in which heating is desired in the present inventive method. Thus, the present invention provides a method of heat treating a patient's prostate tissue wherein the temperature of the prostate tissue is raised from an initial temperature below the destination temperature, to a destination temperature in the range of from 49° C. to almost 57° C. The destination temperature is maintained for a period of time sufficient to administer a sufficient amount of heat to achieve a therapeutic effort on the prostate.

It has now been found that by allowing a patient to acclimatize to elevated urethral temperatures the patient's threshold of pain, with or without anti-inflammatory analgesics, is elevated to about 60° C. Thus, the present invention provides a method of prostatic thermotherapy wherein the maximum urethral temperature is raised to an elevated temperature which exceeds the previous art-accepted maximum by elevating the method temperature in such a manner so as to allow the patient to acclimatize the temperature elevation procedure. The rate at which the temperature can be raised from 37° C. to the range of about 42° C. and 46° C. can be relatively rapid. In keeping with the inventive method, it is desirable for the rate at which temperature is elevated from about 44° C. to the destination temperature to occur more slowly. Further, the rate of rise in temperature preferably decreases as the maximum urethral temperature approaches the destination temperature. In general, the rate of increase in temperature according to the present invention varies between 1° C. per 0.5 minutes to 1° C. per 15 minutes. In order to allow better patient acclimatization, the rate of change in the temperature preferably does not exceed 1° C. per minute, and more preferably does not exceed 1° C. per 2 minutes. However, it is desirable to physician and patient to minimize the amount of time required for therapy. In order to reduce the amount of time required to acclimate the patient to elevated urethral temperatures, the rate of temperature rise can be increased to 1° C. per 10 minutes near the destination temperature and to about 1° C. per 2 minutes at the lower temperatures. The total time to raise the urethral temperatures from 37° C. to the destination temperature preferably ranges from 15 minutes to 2 hours, and more preferably is from 20 to 45 minutes. Moreover, it will be appreciated that the temperature rise can be continuous or discontinuous (i.e., "stepped").

The total amount of heat delivered to the patient is also an important parameter of the present inventive method. While patients are able to acclimate to temperatures up to about 60° C. if the rate of tissue temperature increase is controlled, it is desirable to control the total amount of heat administered to ensure both effective therapy and minimization of side effects. The administration of heat can be quantified by any suitable measurement, however, it is preferable to approximate the quantity of heat administered using the method of Sapareto et al., *International Journal of Radiation Oncology, Biology, Physics*, 10, 787–800 (1984), modified such that the breakpoint of 45° C., rather than 43° C. is used for non-malignant tissues. Thus, while it is only an approximation of the actual thermal dose administered, for the purpose of the present invention, thermal dose measured in equivalent 45° C. hours (or equivalent 45° C. minutes) is equal to the sum of the products of one-half raised to the result of 45 minus the treatment temperature times the duration of time at that temperature, or $$\sum_{t=0}^{t=final} 0.5^{(45-T)} \Delta t,$$

wherein T is temperature in degrees centigrade and t is time in hours (or minutes). For purpose of the present invention, the contribution of temperatures to the thermal dose below 45° C. can be ignored.

Table 1, below, illustrates several heating protocols, (utilized after heating to about 44° C.) that are suitable in the context of the present invention. Each protocol is identified by a letter, A through H. Protocol A defines one preferred embodiment. Protocols B and C define embodiments in which the destination temperature is held for a shorter periods of time, while in the embodiment of protocols D and E the final destination temperature is held for a longer period of time (relative to protocol A). Protocol F defines an embodiment in which the destination temperature is the lowest amongst the illustrated embodiments. Protocol G defines an embodiment in which the destination temperature is higher than the destination temperature of Protocols A–F. Protocol H, which is an operable, but not preferred embodiment of the present invention, illustrates that it is difficult to achieve both pain tolerance (through the use of tolerable rates of temperature increase) and to avoid delivering a thermal dose in excess of about 30,000 equivalent 45° C. minutes (about 500 equivalent 45° C. hours). This is because 1 minute at 60° C. is equivalent to 16,384 equivalent 45° C. minutes, without calculating any temperature ramp time between body temperature and 60° C.

TABLE 1

| Measured Urethral Temperature in Celsius | Time at Measured Temperature in Minutes | | | | | | | |
|---|---|---|---|---|---|---|---|---|
| Protocol: | A | B | C | D | E | F | G | H |
| 44.0 | 1–2 | 1–2 | 1–2 | 1–2 | 1–2 | 1–2 | 1–2 | 1–2 |
| 45.0 | 1 | 1 | 1 | 1 | 1 | 1 | 1 | 1 |
| 45.5 | 1 | 1 | 1 | 1 | 1 | 1 | 1 | 1 |
| 46.0 | 2 | 2 | 2 | 2 | 2 | 2 | 1 | 1 |
| 46.5 | 1 | 1 | 1 | 1 | 1 | 1 | 1 | 1 |
| 47.0 | 2 | 2 | 2 | 2 | 2 | 2 | 2 | 2 |
| 47.5 | 2 | 2 | 2 | 2 | 2 | 2 | 2 | 2 |
| 48.0 | 2 | 2 | 2 | 2 | 2 | 2 | 2 | 2 |
| 48.5 | 2 | 2 | 2 | 2 | 2 | 2 |  | 2 |
| 49.0 | 3 | 3 | 3 | 3 | 3 | 100 | 3 | 3 |

TABLE 1-continued

| Measured Urethral Temperature in Celsius | Time at Measured Temperature in Minutes | | | | | | | |
|---|---|---|---|---|---|---|---|---|
| Protocol: | A | B | C | D | E | F | G | H |
| 49.5 | 2 | 2 | 2 | 2 | 2 | | 2 | 2 |
| 50.0 | 3 | 3 | 3 | 3 | 3 | | 3 | 3 |
| 50.5 | 2 | 2 | 2 | 2 | 2 | | 2 | 2 |
| 51.0 | 45 | 20 | 30 | 75 | 90 | | 3 | 3 |
| 51.5 | | | | | | | 3 | 3 |
| 52.0 | | | | | | | 3 | 3 |
| 52.5 | | | | | | | 3 | 3 |
| 53.0 | | | | | | | 4 | 4 |
| 53.5 | | | | | | | 3 | 3 |
| 54.0 | | | | | | | 4 | 4 |
| 54.5 | | | | | | | 3 | 3 |
| 55.0 | | | | | | | 4 | 4 |
| 55.5 | | | | | | | 4 | 4 |
| 56.0 | | | | | | | | 4 |
| 56.5 | | | | | | | . | 5 |
| 57.0 | | | | | | | . | 4 |
| 57.5 | | | | | | | | 4 |
| 58.0 | | | | | | | | 5 |
| 58.5 | | | | | | | | 4 |
| 59.0 | | | | | | | | 5 |
| 59.5 | | | | | | | | 4 |
| 60.0 | | | | | | | | 5 |
| Approximate Thermal Dose (eqv. 45° C. hrs.): | 54 | 27 | 38 | 86 | 102 | 28 | 300 | 4160 |
| Approximate Thermal Dose (eqv. 45° C. min.): | 3230 | 1630 | 2270 | 5150 | 6110 | 1670 | 40600 | 249,600 |

Preferably, the gradual increase in temperature is automatically regulated. Accordingly, for electromagnetic radiating catheters, it is preferable for the power source that provides the energy to the radiation applicator be in operable association with urethral temperature sensors by way of a microprocessor, computer, or the like. Similarly, for heating catheters (e.g., hot water heaters) it is preferable for an automatic regulator to control the temperature of the catheter positioned in the prostatic urethra.

The present invention also provides a surprisingly effective form of thermotherapy of the prostate. Prior art methods have called for maximum treatment temperatures at about 47° C. or lower ("low temperature treatments") or at temperatures well in excess of 60° C. ("high temperature treatments"). However, thermotherapy according to the present invention is advantageously conducted at a temperature of from 49° C. to about 57° C., and preferably, at a temperature of from about 50° C. to about 55° C. It will be appreciated that in a prostate in which the tissue temperature sensor measures a temperature of 51° C. to 52° C. that the actual range of temperatures in the heated tissue will vary and in isolated places can reach temperatures as high as 55° C. Tissue temperature variation is consequence of uneven dispersion of energy from the antenna or heating portion of the catheter, differential absorption of the dispersed energy by the targeted tissue, and variations in blood perfusion through the target tissue. Blood, of course, will be about 37° C. in a human and acts as coolant. Preferably patient tissue is heated to a maximum average sensed temperature of about 51° C. to about 52° C.

Thermotherapy conducted in this temperature range is more effective than that conducted at the lower temperature ranges and is not accompanied by an increase in side-effects (except for the need to anesthetize the patient with medication or acclimate the patient by gradually increasing urethral temperatures). Moreover, thermotherapy of the prostate performed in accordance with the present invention is accompanied by substantially fewer side effects such as, for example, hematuria, dysuria, tissue slough, retrograde ejaculation, extended catheterization and the like; see De La Rosette et al., supra than thermotherapy performed at temperatures exceeding 60° C.

The temperature of the prostate is maintained at the destination temperature (regardless of whether the temperature is gradually or rapidly increased to the destination temperature) for a period of time suitable to effect a therapeutic result (e.g., a decrease in the AUA symptom score). Suitable times at the treatment temperature can be as short as about 0.5 minutes, but are preferably at least 30 minutes. Suitable times at the treatment temperature can be as long as desired, but in order to avoid overdosage of heat, undesirable side effects, and loss of time, the time at the treatment temperature can be as long as about 4 hours, but preferably is not longer than about 2 hours, and more preferably is not longer than about 1 hour. Treatment time should take into account the thermal dose that is administered.

Heat treatment according to the present invention preferably provides the urethra proximal tissues with a heat dose that is sufficient to provide a therapeutic effect, but which is low enough to avoid excessive undesired side-effects. For example, treatment according to the present invention provides at least an estimated minimum cumulative thermal dose of at least about 1500 equivalent 45° C. minutes (i.e., 25 equivalent 45° C. hrs.). More preferably, treatment according to the present invention provides at least about 2000 equivalent 45° C. minutes. Treatment according to the present invention preferably provides an estimated maximum cumulative thermal dose which does not exceed about 30,000 equivalent 45° C. minutes, and more preferably does not exceed about 20,000 equivalent 45° C. minutes, and yet more preferably does not exceed about 7000 equivalent 45° C. minutes.

The present inventive method is specifically designed to provide the highest temperatures in the prostatic urethra consistent with minimizing side effects and patient discomfort. The method is preferably accomplished in a straightforward method by not using a cooled catheter. A cooled catheter causes the peak temperatures to occur a well within the prostate away from the urethral walls. When a cooled catheter is used, measured tissue temperatures decline rapidly as the urethra is approached, such that the 2 mm of prostate tissue proximal to the urethra typically do not receive therapeutic quantities of heat. However, rather than attempting to insulate these tissues, the present invention seeks to directly treat these tissues. When a heating catheter or non-cooled electromagnetic-radiating catheter is used the highest temperatures are reached in the urethra. Temperature declines deeper into the prostate tissue away from the catheter. Surprisingly, this heating pattern provides substantially more effective treatment.

Moreover, high temperature prior art techniques have focused on ablation of deep prostate tissue with the idea that eliminating deep prostatic tissue mass would decrease the pressure on the urethra allowing better urine flow and other benefits. In contrast, the present inventive method does not have the goal of decreasing prostate volume or mass and substantial changes in prostate volume or mass are not an expected outcome of the present inventive therapy. While applicants do not wish to be bound to any particular theory, it is believed that the application of an appropriate dose of heat to the prostatic urethra and the urethrally proximal prostate tissue causes a change in sensation. It is not known whether this change in sensation is accompanied by physical changes to the nerve bundles extending along the urethra through the prostate, but it is conceivable that these neurons are the true targets of the thermotherapy. In any event, while it is possible to use a catheter with a cooling device to practice the present invention, there is not a compelling medical reason to do so.

By limiting all tissue temperatures to less than about 57° C., and preferably less than about 55° C., the substantial side-effects accompanying very high temperature thermal therapy are advantageously avoided. Treatment according to the present invention is not unduly or intolerably painful. However, pain relieving medication can be optionally administered. Preferably, treatment according to the present invention does not require narcotic analgesics, however, the use of anti-inflammatory analgesics and mild anxiolytics can be administered according to the judgement of the skilled clinician.

Figure 2:
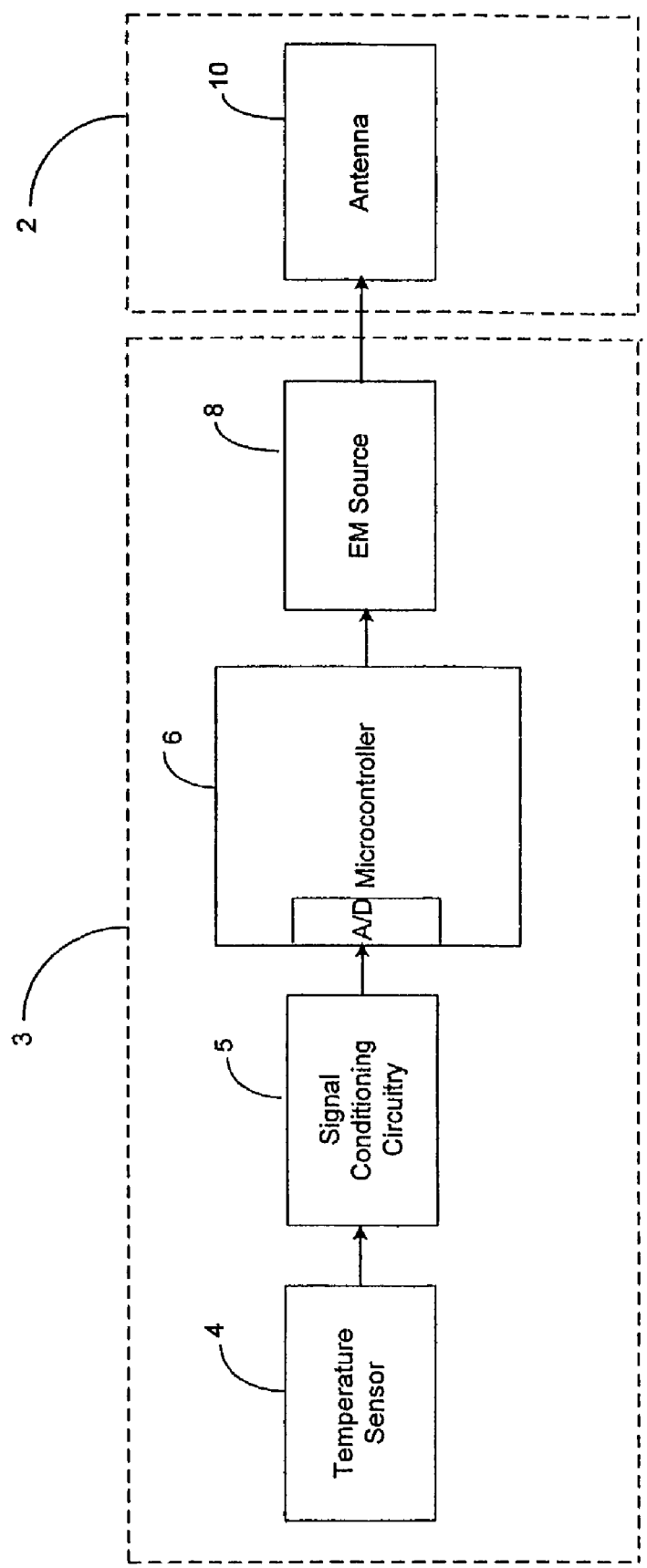
FIG. 2 is a block diagram of the temperature control system and the microwave applicator of the system illustrated in FIG. 1.

One aspect of the present invention provides a urethral insertable electromagnetic radiation applicator system suitable for implementing the present inventive method. FIG. 1 provides a block diagram of an example of a urethral insertable electromagnetic radiation applicator system according to an embodiment of the present invention. The system includes a catheter 1 for insertion into the urethra. The catheter 1 generally is adapted to enclose a microwave applicator 2. As illustrated in FIG. 2, the microwave applicator includes an antenna 10 for radiating electromagnetic energy through the wall of the catheter to body tissue, particularly a prostate gland undergoing treatment.

In this embodiment, the catheter 1 and the microwave applicator 2 may be variously configured, and can be similar to the catheter and the applicator disclosed in U.S. Pat. No. 4,967,765, the disclosure of which is hereby incorporated by reference in its entirety. In the referenced document, the microwave applicator includes a helical coil antenna mounted inside a urethral catheter. A suitable electrical connector, such as a coaxial cable connects the antenna to external excitation electronics. The antenna delivers electromagnetic radiation through the wall of the catheter to heat tissue adjacent to the catheter. Using a helical coil antenna is preferred to provide substantially uniform heating along the length of the antenna.

According to an important aspect of the invention, the applicator system includes a temperature control system 3 for regulating the temperature of tissue heated by the microwave applicator 2. Although the temperature control system may be an open loop system or a closed loop system, in a preferred embodiment, the temperature control system 3 comprises a closed loop system. In a most preferred embodiment, the temperature control system senses the temperature of tissue to being heated by the microwave applicator and regulates the electromagnetic energy output by the microwave applicator based on the sensed tissue temperature. Regulating the electromagnetic energy output by the microwave applicator based on the sensed tissue-temperature is preferred, because the tissue temperature may be a non-linear function of applied electromagnetic energy. More particularly, when electromagnetic energy is applied-to tissue, such as the tissue of the prostate gland, the resulting temperature of the tissue depends on a variety of factors, for example, the blood flow to the tissue. Moreover, the relationship between temperature and applied electromagnetic energy may vary from one patient to the next. In conventional systems, the power applied to microwave applicators was simply increased in fixed power increments. For example, the power was increased by x watts every y minutes. Such a system is less preferred because of the variable relationship between applied electromagnetic energy and tissue temperature. Thus, by controlling the applied electromagnetic energy based on an accurately sensed temperature, embodiment of the present invention are capable of accurately regulating tissue temperature, while accounting for variations in the tissue being heated.

FIG. 2 illustrates an example of a block diagram of the temperature control system 3 and the microwave applicator 2 according a preferred embodiment of the invention. In the illustrated embodiment, the temperature control system 3 comprises a temperature sensor 4 capable of sensing tissue temperature, signal conditioning circuitry 5 for conditioning the output signal from the temperature sensor 4, a microcontroller 6 for producing a temperature control signal based on the output signal from the temperature sensor 4, and an electromagnetic energy source 8 for applying electromagnetic energy to the antenna 10. The components illustrated in FIG. 2 cooperate to control the temperature of tissue being treated in response to the sensed tissue temperature.

The temperature sensor 4 may be variously configured. For example, the temperature sensor 4 may comprise a thermistor or thermocouple capable of sensing the temperature of tissue, such as the tissue of the prostate gland. In an alternative embodiment, the temperature sensor 4 may comprise a resistance temperature difference (RTD) sensor. The temperature sensor 4 preferably produces an output signal, e.g., a voltage, indicative of the tissue temperature.

The signal conditioning circuitry preferably receives the output signal from the temperature sensor and conditions the signal for processing by the microcontroller 6. For example, the signal conditioning circuitry may include a low-pass filter for filtering noise from the signal from the temperature sensor 4. The signal conditioning circuitry may also include an amplifier, such as an operational amplifier, for amplifying the signal output from the temperature sensor 4. The gain of the operational amplifier is preferably selected so that the voltage range of the output signal of the signal conditioning circuitry matches the input voltage range of the microcontroller 6.

The microcontroller 6 may be variously configured. For example, the microcontroller 6 may comprise a microprocessor including internal memory circuits and analog to digital conversion circuitry, for processing the output signal from the signal conditioning circuitry and producing the temperature control signal. Although the illustrated embodiment depicts a microcontroller having an internal analog to digital converter, the present invention is not limited to such an embodiment. For example, the analog to digital converter may be external to the microcontroller 6. A temperature control program controls the microcontroller to output the temperature control signal based on the sensed tissue temperature. The temperature control program may be stored in memory internally or externally to the microcontroller. In an alternative embodiment, the temperature control program may be stored in a portable computer-readable storage medium, such as a magnetic disk or an optical disk. Utilizing a temperature control program to produce the control signal is preferred because the program can be updated as treatment protocols, e.g., treatment temperatures and/or durations, change.

The present invention is not limited to utilizing a microcontroller 6 to produce the temperature control signal. For example, analog or digital circuitry that performs equivalent functions to the microcontroller or the temperature control program is within the scope of the invention.

An electromagnetic energy source 8 receives the temperature control signal from the microcontroller and applies electromagnetic energy to the antenna. In a preferred embodiment, the electromagnetic energy source comprises an oscillator. The frequency of oscillation of the oscillator is preferably selected for optimal heating of tissue within FCC regulations. The oscillation frequency of the electromagnetic energy source is preferably selected to be about 915 MHz or about 12, in accordance with present FCC regulations. However, the present invention is not limited an oscillation frequency of 915 MHz. For example, if another frequency is determined to be more therapeutically beneficial and/or FCC regulations change, the preferred frequency of oscillation may change accordingly.

The antenna 10 receives the electromagnetic energy from the source 8 and radiates the energy to the tissue being treated. As stated above, the antenna preferably comprises a helical coil antenna. However, the present invention is not limited to helical coil antennas. Any antenna that produces a substantially uniform radiation pattern over a desired area of treatment is within the scope of the invention.

Figure 3:
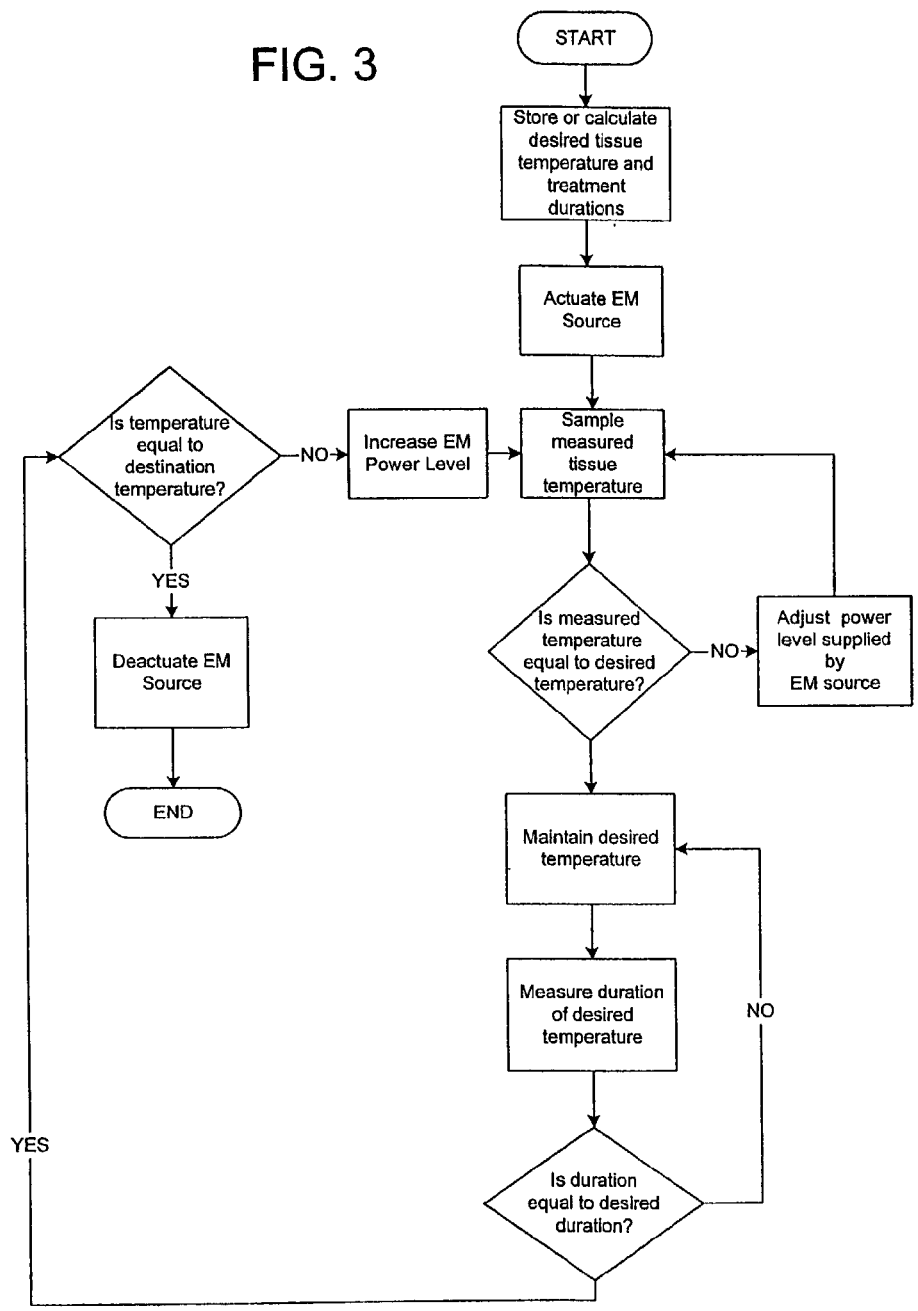
FIG. 3 is a flow chart of a temperature control program for regulating the temperature of body tissue heated by the microwave applicator of FIG. 2.

FIG. 3 is a flow chart of an example of a temperature control program according to an embodiment of the present invention. Once the catheter 1 is inserted into the urethra and the antenna is positioned near the prostate gland, the electromagnetic energy source is actuated. In order to avoid having to anesthetize the patient, the program preferably increases the temperature in predetermined or specified increments and maintains the temperature at each increment for a predetermined or specified duration. The temperature control program may store or calculate a plurality of desired prostatic tissue temperatures and a treatment duration corresponding to each temperature. The temperature sensor measures the tissue temperature. The control program may sample the measured temperature and store the measured temperature in memory. The program determines whether a first desired temperature level for treatment has been reached, i.e., by comparing the measured temperature stored in memory to one of desired treatment temperatures. If the first temperature has not been reached, the microcontroller continues increasing the temperature. Once the first temperature has been reached, the microcontroller adjusts the temperature control signal to maintain the first temperature. In order to maintain the first temperature, the microcontroller adjusts the temperature control signal based on the output signal from the temperature sensor, i.e., by sampling and comparing the measured temperature to the first desired temperature.

According to a preferred embodiment, the microcontroller also measures and controls the duration of treatment at each desired temperature. This measurement may be performed by executing a timer routine once each desired temperature is reached. The timer routine records the duration of the treatment at each desired temperature. The program compares the recorded duration to a desired duration. Once the desired duration has been reached, the program continues to the next processing step. In an alternative embodiment, an external timer circuit may be coupled to the microcontroller to measure treatment duration.

Once treatment occurs at a first desired temperature for a first desired time period, the control program determines whether the first temperature is the final or destination temperature in the processing routine. If the first temperature is the final or destination temperature, the program deactuates the electromagnetic energy source and ends. However, because the treatment preferably occurs at a plurality of different temperature levels, the temperature control program preferably increases the power level after the treatment at the first temperature so that treatment can occur at a second at a second temperature, preferably higher than the first temperature. The control program preferably repeats these steps, i.e., increasing the temperature until a desired temperature is reached, maintaining the temperature at the desired temperature for a desired duration, then increasing the temperature to the next level. Because the power level is controlled based on the sensed tissue temperature, the control program automatically tailors itself to each patient.

As stated above, the control program preferably steps through a plurality of temperature levels with predetermined or specified durations. The predetermined or specified durations may be fixed or variable. The number of levels, the temperature at each level, and the duration of each level are preferably selected to reduce patient discomfort and increase the effectiveness of treatment. In a most preferred embodiment, the temperature levels and durations are selected as shown in Table 1 above.

As illustrated in Table 1, a preferred embodiment of the treatment protocol begins at 44° C. In order to reach a tissue temperature of 44° C., the control program may actuate the electromagnetic source at an initial level until 44° C. is reached. The program may increase the temperature in predetermined or specified steps, as illustrated in FIG. 3 in order to reach 44° C. In an alternative embodiment, since the low temperature portion, e.g., between about 37° C. and about 44° C., of the treatment protocol is not as important, the control program may actuate the electromagnetic energy source such that the antenna delivers one watt during each 30 second time internal until 44° C. is reached. Once 44° C. is reached, the temperature control program preferably controls the energy applied by the antenna based on the sensed tissue temperature as illustrated in Table 1. For example, when the tissue temperature measured by the temperature sensor is 44° C., the microcontroller executes a timer routine. When the timer routine reaches 1 minute, the microcontroller preferably increases the power applied by the electromagnetic energy source to increase the tissue temperature to the next level, e.g., 44.5° C. When the tissue temperature measured by the temperature sensor reaches 44.5° C., the microcontroller preferably maintains that level and re-executes the timer routine. In this manner, the microcontroller and the temperature sensor step through the desired treatment protocol. Because the temperature increments according to Table 1 are relatively small, e.g., about 0.5 degrees, the patient is able to acclimate to the elevated temperatures, discomfort is minimized, and the need for narcotic analgesics and/or general anesthesia is attenuated or eliminated.

Once the destination temperature is reached and maintained for a desired time period, the control program deactuates the electromagnetic energy source and ends. According to Table 1, the destination temperature is preferably 51° C. and the treatment duration at that temperature is 45 minutes. However, the present invention is not limited to a destination temperature of 51° for a duration of 45 minutes. For example, the destination temperature is preferably between 49° C. and about 57° C., and more preferably between about 50° C. and about 55° C. Also, the average maximum sensed temperature is between about 51° C. and about 52° C. The treatment duration at the destination temperature preferably does not exceed about 60 minutes.

The present invention is not limited to the temperature below the destination temperature or the durations at these temperatures illustrated in Table 1. For example, the control program may control the tissue temperatures such that the temperature is increased in increments of about 1° C. The treatment duration at each temperature is preferably selected to range from no less than about 30 seconds to no more than about 15 minutes, and more preferably no less than about 1 minute to no more than about 10 minutes, and even more preferably no less than about 2 minutes to no more than about 5 minutes. The longer the duration at each temperature, the lower the discomfort level of the patient. On the other hand, increasing the duration also increases treatment time. Thus, the upper limit of about 15 minutes per degree is preferably not exceeded.

Although increasing the temperature in predetermined or specified steps is preferred, the present invention is not limited to such an embodiment. For example, the control program may implement a slow ramping function from an initial temperature to a destination temperature. The initial temperature may be about 37° C. The destination temperature may be about 51° C. In order to implement the ramping function the temperature control program may actuate the electromagnetic energy source. The temperature sensor measures the tissue temperature. The temperature control program may sample and store values corresponding to the measured temperature. The control program may determine the rate of change of the temperature signal, i.e., by differentiating the temperature signal utilizing the stored values. The control program may compare the calculated rate of change to a desired rate of change. If the rate of change in temperature is greater than the desired rate of change, the temperature sensor decreases the energy supplied by the electromagnetic energy source. If the rate of change in temperature is less than the desired rate of change, the temperature sensor decreases the power supplied by the electromagnetic energy source. If the rate of change is less than a desired rate of change, the temperature control program increases the energy supplied by electromagnetic energy source. The desired rate of increase in temperature may be fixed or variable. Once the destination temperature is reached, the temperature control program preferably maintains the destination temperature for a predetermined or specified time period, as described above.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A computer program product comprising a computer-usable medium having program logic for controlling an electromagnetic energy applicator in a urethral catheter, the computer program product comprising:

temperature setting program code for programming desired prostatic tissue temperature values, each of said values being lower than a subsequent value;

temperature determining program code for determining and measuring a temperature value of prostatic tissue;

temperature comparing program code for comparing the measured prostatic tissue temperature value to the programmed prostatic temperature values; and control signal adjustment program code for adjusting a power control signal to vary prostatic tissue temperature in accordance with a relationship between the measured prostatic tissue temperature and the programmed prostatic tissue temperature values depending on the time the prostatic tissue has been at the measured prostatic tissue temperature, wherein the prostatic tissue temperature is first maintained at a first temperature value for a first set time period sufficient for acclimatizing the patient and is then increased to subsequent programmed temperature values for periods of time sufficient to achieve a therapeutic effect on the prostate.

2. The computer program product of claim 1 wherein the first desired prostatic tissue temperature value ranges from about 42° C. to about 46° C. and the second desired prostatic tissue temperature value ranges from about 49° C. to about 60° C.

3. The computer program product of claim 1 wherein the first and second set time periods are each no less than about thirty seconds.

4. A computer operatively connected to an apparatus for treating prostate tissue for benign prostatic hyperplasia or prostatitis in a patient having a urethra, said apparatus including a catheter for insertion into the urethra, and an applicator within the catheter and a connector for connecting the applicator to an energy source, wherein the computer embodies a program of instructions executable by the computer for performing the steps of:

establishing a value of power from said energy source to be applied by said applicator;

determining a value of temperature of the prostate tissue;

adjusting said power from said energy source in dependence on the time the prostate tissue has been at said prostate tissue temperature value; and computing a value of thermal dosage of said prostate tissue that is a function of said prostate tissue temperature value and the time said prostate tissue has been at said prostate tissue temperature value.

5. The computer of claim 4 wherein said thermal dosage value computation step further comprises a function including the product of said prostate tissue temperature and the time said prostate tissue has been at said prostate tissue temperature value.

6. The computer of claim 4 wherein the program further comprises instructions executable by the computer for performing the step of computing a cumulative value of said thermal dosage corresponding to the sum of the values of said thermal dosage at a plurality of values of said prostate tissue temperature.

7. The computer of claim 4 wherein the program further comprises instructions executable by the computer for performing the step of determining a therapeutic effect on said prostate tissue in dependence on a value of said cumulative thermal dosage.

8. The computer of claim 7 wherein the program further comprises instructions executable by the computer for performing the step of correlating said therapeutic effect to a value of prostate tissue necrosis.

9. The computer of claim 6 wherein the program further comprises instructions executable by the computer for performing the steps of selecting said value of said cumulative thermal dosage to be a thermal dose of about 1500 equivalent 45° C. minutes to about 30,000 equivalent 45° C. minutes is applied to the prostate tissue proximate the applicator.

10. The computer of claim 4 wherein the program further comprises instructions executable by the computer for performing the steps of generating control signals for said applicator to apply to the prostate tissue proximate said applicator a thermal dose of about 1500 equivalent 45° C. minutes to about 30,000 equivalent 45° C. minutes.

11. The computer of claim 4 wherein the program further comprises instructions executable by the computer for performing the step of generating signals indicative of a distribution of said applied power in said tissue proximate to said applicator.

12. A computer operatively connected to an apparatus for treating prostate tissue for benign prostatic hyperplasia or prostatitis in a patient having a urethra, said apparatus including a catheter for insertion into the urethra, and an applicator within the catheter and a connector for connecting the applicator to an energy source, wherein the computer embodies a program of instructions executable by the computer for performing the steps of:
establishing a value of power from said energy source to be applied by said applicator;
determining a value of temperature of the prostate tissue;
adjusting said power from said energy source in dependence on the time the prostate tissue has been at said prostate tissue temperature value; and
generating signals corresponding to a distribution of energy delivered to the tissue proximate to the applicator radially away from and along a length of the applicator.

13. The computer of claim 12 wherein said energy distribution generation step further comprises the step of generating signals corresponding to a Specific Absorption Rate of power in said tissue.

14. A computer program product comprising a computer-usable medium having program logic for controlling an electromagnetic energy applicator in a urethral catheter, the computer program product comprising:
temperature setting program code for establishing a plurality of desired prostatic tissue temperature values building to a final desired temperature;
temperature determining program code for determining and measuring a temperature value of prostatic tissue surrounding a distal end of the catheter;
temperature comparing program code for comparing the measured prostatic tissue temperature value to each of the plurality of desired prostatic temperature values;
control signal adjustment program code for adjusting a power control signal to vary prostatic tissue temperature in accordance with a relationship between the measured prostatic tissue temperature and each of the plurality of desired prostatic tissue temperatures depending on the period of time the prostatic tissue has been at the measured prostatic tissue temperature;
wherein said control signal adjustment program code also controls the duration for which each of said plurality of desired prostatic tissue temperature values are maintained via said power control signal, prior to said measured prostatic tissue temperature value meeting said final desired temperature, wherein at least one of the plurality of desired prostatic tissue temperature values and the duration thereof is set for achieving a therapeutic effect on the prostate.

15. A computer program product comprising a computer-usable medium having program logic for controlling an electromagnetic energy applicator in a urethral catheter for prostatic thermotherapy, the computer program product comprising:
temperature setting program code for establishing a temperature range and a final temperature, said final temperature being outside and greater than the temperature range;
temperature comparing program code for comparing a measured prostatic tissue temperature value to the temperature range and to the final temperature;
control signal adjustment program code for adjusting a power control signal to the applicator in accordance with the comparison between the measured prostatic tissue temperature value and the temperature range and final temperature depending on the time the prostatic tissue has been at the measured prostatic tissue temperature value, wherein the measured prostatic tissue temperature value is first maintained within the temperature range for a first predetermined lime period sufficient to achieve a first therapeutic effect on the prostate and is then maintained at the final temperature for a second predetermined time period s sufficient to achieve a second therapeutic effect on the prostate.

* * * * *

UNITED STATES PATENT AND TRADEMARK OFFICE
CERTIFICATE OF CORRECTION

| | | |
|---|---|---|
| PATENT NO. | : 7,089,064 B2 | Page 1 of 1 |
| APPLICATION NO. | : 10/232062 | |
| DATED | : August 8, 2006 | |
| INVENTOR(S) | : Charles F. Manker et al. | |

It is certified that error appears in the above-identified patent and that said Letters Patent is hereby corrected as shown below:

Front page, after "Related U.S. Application Data" delete from "(62) Division of application" to "Pat. No. 6,522,931." and insert the following:
-- (62) Division of application No. 09/766,746, filed on January 22, 2001, now Pat. No. 6,522,931, which is a continuation of application No. 09/130,708, filed on August 6, 1998, now Pat. No. 6,216,703 and provisional application No. 60/084,714, filed on May 8, 1998. --.

Column 1, line 9, change "6,522,391" to -- 6,522,931--.

Column 1, line 11, after "herein by reference in its entirety," delete "." and insert the following:
-- , which is a continuation of U.S. patent application Ser. No. 09/130,708, filed on August 6, 1998, now Pat. No. 6,216,703, which claims the benefit of U.S. Provisional Application Ser. No. 60/084,714, filed on May 8, 1998. --.

Claim 15, line 52, "lime" should be -- time --.

Claim 15, line 55, delete "s."

Signed and Sealed this

Third Day of April, 2007

JON W. DUDAS
*Director of the United States Patent and Trademark Office*